United States Patent [19]

Cairns et al.

[11] 4,110,625

[45] Aug. 29, 1978

[54] METHOD AND APPARATUS FOR MONITORING THE DOSE OF ION IMPLANTED INTO A TARGET BY COUNTING EMITTED X-RAYS

[75] Inventors: James Anthony Cairns, Wantage, England; Allen Lurio, Dobbs Ferry; James Francis Ziegler, Putnam Valley, both of N.Y.

[73] Assignee: International Business Machines Corporation, Armonk, N.Y.

[21] Appl. No.: 752,779

[22] Filed: Dec. 20, 1976

[51] Int. Cl.² ............................................. A61K 27/02
[52] U.S. Cl. ............................... 250/492 A; 250/272; 250/492 B
[58] Field of Search ............... 250/492 A, 272, 492 B; 357/91

[56] References Cited

U.S. PATENT DOCUMENTS

| | | | |
|---|---|---|---|
| 3,563,809 | 2/1971 | Wilson | 250/492 A |
| 3,573,454 | 4/1971 | Andersen | 250/492 A |
| 3,699,334 | 10/1972 | Cohen et al. | 250/492 A |

*Primary Examiner*—Harold A. Dixon
*Attorney, Agent, or Firm*—Michael J. Weins; Bernard N. Wiener; Murray Nanes

[57] ABSTRACT

Practice of this disclosure obtains a measure of the dose or fluence of implanted ions into a target for device fabrication by monitoring emitted X-rays. Illustratively, ion beams of $B^+$, $P^+$ or $As^+$ have been implanted into Si over the ion energy range of 20 KeV to 2800 KeV and the data of counts of emitted X-rays has been correlated with both the solid angle intercepted by the counter and the charge intercepted by the target. In particular, the low energy soft Si(L) X-rays at 136Å have been discovered for the practice of this disclosure to be very intense. The principles of this disclosure are especially applicable for very low ion doses, i.e. $\lesssim 10^{12}/cm^2$ where charge integration is not feasible; and for neutral beam implantation with currents above about 2 milliamperes. Reproducible semiconductor devices can be fabricated by practice of this disclosure, i.e., with substantially reproducible operational characteristics, e.g., bipolar and field-effect transistors with silicon integrated circuit technology.

12 Claims, 8 Drawing Figures

METHOD AND APPARATUS FOR MONITORING THE DOSE OF ION IMPLANTED INTO A TARGET BY COUNTING EMITTED X-RAYS

BACKGROUND OF THE INVENTION

Ion implantation has been utilized for the introduction of impurities into a substrate because it is a "cold" technology (which does not require the material degrading heat cycles necessary for thermal diffusion masks, and the diffusion itself), and because it is a technology whereby reproducible results can be obtained. Devices so fabricated are substantially reproducible even if the flux of the ion beam should vary significantly with time, provided only that the ion beam current can be accurately monitored to obtain the total implant dose. It has been difficult heretofore to measure beam current for very low levels of implanted impurities (doses $\lesssim 10^{12}$ atoms/cm$^2$) because the current may be of the order of $10^{-10}$ Amperes. For example, such low dose may be used for shifting the threshold of a field-effect transistor.

Other applications require very high impurity doses. Some accelerators commonly used for ion implantation can deliver currents above $10^{-2}$ amperes for very high levels of implanted impurities. A charge-neutral beam can be obtained by introducing electrons into the beam which keep it from dilating due to space-charge effects. However, these high current ion implantations may be accompanied by inaccurate current monitoring because of the electrons put into the beam.

Recently, in the literature of ion implantation for device fabrication, the problem of reproducibility of the dose of implanted ions has been addressed by making use of information concerning the spatial position of the beam on the substrate together with measurement of the instantaneous current to the target which allowed a final correction to be made to those areas which had received too little dose. There has also been a suggestion in the literature that monitoring of the substrate temperature could aid in the fabrication reproducibly of semiconductor devices through use of ion implantation.

The following literature articles are identified as being of background interest concerning use of X-rays emitted as a consequence of ions impinged upon a substrate for a technological purpose:

(1) W. Beezhold et al. in Applied Phys. Letters 21, 592, (1972) describes a study of ion-induced X-rays from H and He bombardment to detect charge build-up on an insulating surface.

(2) H. Kamada et al. in "6th Conference on X-ray Optics and Microanalysis," p 541, Univ. of Tokyo Press 1972 describe spectrochemical analysis by study of low energy ion-induced X-rays.

OBJECTS OF THE INVENTION

It is an object of this invention to provide a method for monitoring the dose of ions implanted into a substrate during fabrication of a device by monitoring X-rays, including both high energy and low energy soft X-rays emitted from the incident ions or induced from atoms of the substrate. Heretofore the use of the term x-rays unless otherwise qualified shall mean x-ray in the generic sense and include high energy x-rays and low energy soft x-rays.

It is another object of this invention to fabricate reproducibly silicon semiconductor devices by implanting ions of B$^+$, P$^+$, or As$^+$ and concomitantly monitoring externally the X-rays developed in the substrate as consequence of the implanting ions as a measure of the ion dose.

It is another object of this invention to provide technology for monitoring dose of ions from ion implantation when charge integration is not feasible.

It is another object of this invention to provide technology for monitoring the dose of ions from ion implantation for low doses and for neutral beams.

SUMMARY OF THE INVENTION

It has been discovered for the practice of this invention that the X-rays produced during the ion implantation by ion-solid interaction can be used to monitor the implantation dose of ions. X-rays either from the ions or from the substrate may be monitored. The number of X-rays produced can be related to the number of incident ions for evaluation of how many ions have been implanted into the substrate. Through monitoring of X-rays emitted from the atoms of the substrate per se, a single detector can be used for monitoring the dose of implantations of various ions.

Practice of this invention obtains a measure of the dose or fluence of implanted ions into a target for device fabrication by monitoring emitted X-rays. Illustratively, ion beams of B$^+$, P$^+$ or As$^+$ have been implanted into Si over the ion energy range of 20 KeV to 2800 KeV and the data of counts of emitted X-rays has been correlated with both the solid angle intercepted by the counter and the charge intercepted by the target. In particular, the Si(L) soft X-rays at 136A have been discovered for the practice of this invention to be very intense. The principles of this invention are especially applicable for very low ion doses, i.e., $\lesssim 10^{12}$/cm$^2$, where charge integration is not feasible, and for neutral beam implantation with current above about 2 milliamperes. The fabrication of a sequence of comparable semiconductor devices is accomplished by practice of this invention, i.e., with substantially reproducible operational characteristics, e.g., a plurality of bipolar or field-effect transistors with silicon integrated circuit technology.

DRAWINGS FOR THE INVENTION

FIGS. 2 and 3 are graphical presentations of actual data on emitted X-rays expressed as number of X-ray counts per msr per $\mu$C versus ion energy into silicon for implanted As$^+$, B$^+$, and P$^+$, where msr = millisteradian and $\mu$C = microcoulomb, wherein: FIG. 2 presents data for relatively high energy X-rays; and FIG. 3 presents data for relatively low energy soft X-rays.

PRACTICE OF THE INVENTION

Figure 1A:
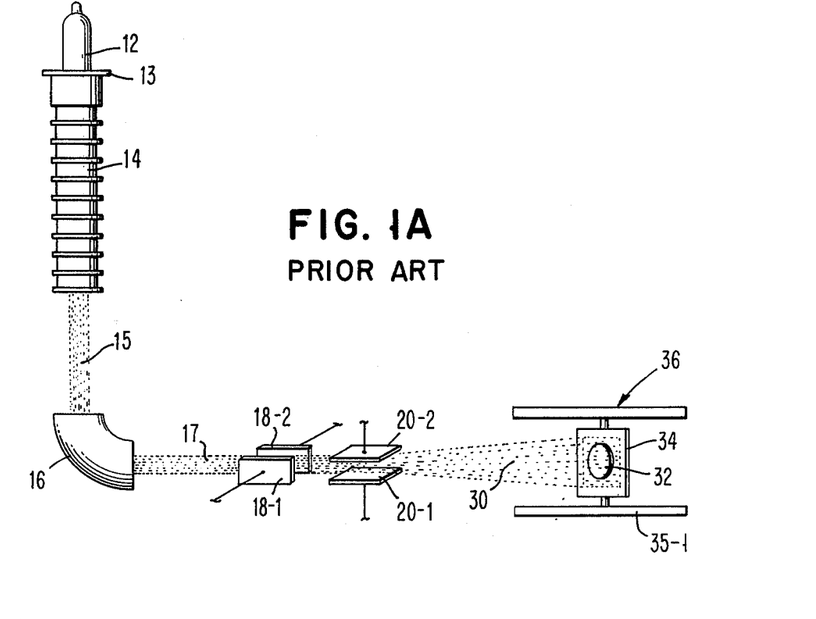
FIG. 1A shows the essential features of an ion accelerator suitable for generating and for implanting ions in a target for practice of this invention.

FIG. 1A is an illustration in schematic form of an accelerator apparatus in the nature of the prior art suitable for ion implantation into a target layer in accordance with the principles of this invention. The basic elements of the apparatus include an ion source 12 mounted on the end 13 of an accelerator unit 14. Ions 15 emerge from the accelerator tube 14 and pass through a momentum analyzing magnet 16. The ion beam 17 which emerges from the analyzing magnet 16 passes through an ion deflection system which comprises horizontal beam scanner plates 18-1 and 18-2 vertical beam scanner plates 20-1 and 20-2. The ion beam 30 emerges from the beam scanner plates and is directed upon the target 32 which is mounted on plate 34 which is constrained by mount 36.

The X-rays produced during bombardment of silicon wafers by exemplary ion beams of $B^+$, $P^+$, and $As^+$ at energies from 20-2800 KeV have been evaluated experimentally for the practice of this invention.

Figure 1B:
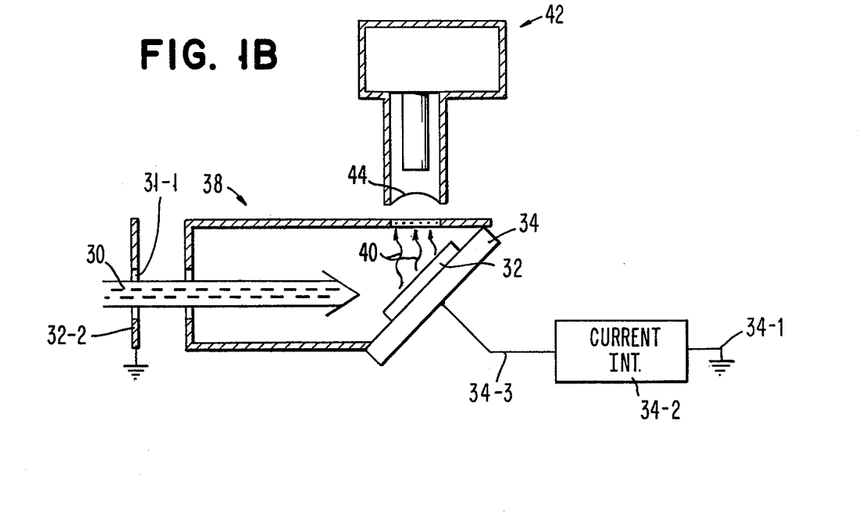
FIG. 1B shows certain details of an ion implantation target chamber with a flow proportional counter detector for X-rays emitted from a target caused by ions implanted therein from the accelerator shown in FIG. 1A.

The experimental arrangement at the region of the target is shown in greater detail in FIG. 1B in the nature of the prior art. The ion beam 30 enters a long Faraday cup 38 via the opening 31-1 in grounded metal collimator plate 31-2 and strikes the target 32. The target 32 on mount 34 is tilted at 45° to the beam to minimize ion beam channeling, and to allow the X-rays 40 to escape to the detector 42. The target 32 is electrically connected to ground 34-1 via connector 34-3 and coulomb charge detector 34-2, which is conveniently a current integrator.

The detector 42 for detecting emitted soft X-rays comprises a flow proportional counter with an entrance window 44 of 1 micrometer stretched polypropylene with a conducting Al layer on its surface inside of the detector 42. Such a detector is described by J. A. Cairns et al. in Nucl. Instr. and Meth., 88, 239 (1970). The window 44 is thin enough easily to allow detection of the low energy soft Si(L) X-rays with energy of 91 ev. A series of filters, not shown, can be placed in front of the detector 42 because the actual X-ray flux can vary over seven orders of magnitude dependent upon ion current and X-ray cross-section. The filters can be apertures which allow the solid angle of detector 42 to be changed from 0.005 msr to 22 msr (millisteradians). The detector gas may conveniently be methane plus argon flowing at atmospheric or subatmospheric pressure at a rate of 0.04 ft$^3$/hour. The detector voltage may readily be kept in the range of 2-2.2 kV.

For an exemplary practice of this invention the one micrometer polypropylene window 44 was sufficiently thick to stop penetration of most heavy ions below 500 keV into the active region of the detector 42. For more energetic ions it was necessary to add another layer of polypropylene to the detector entrance window. This additional layer reduced the Si(L) X-rays detected. However, at these energies, the higher energy Si(K) yield was not significantly affected by the second layer and was adequate for most current monitoring applications.

Data was also taken with a Si(L) detector for measurements with ion beams above 300 keV. The As(L), Si(K), and P(K) X-rays were all clearly resolved and permitted extrapolation to the unresolved flow proportional counter data. The flow proportional counter easily separated these high energy X-rays from the low energy soft Si(L) X-rays.

Figure 2:
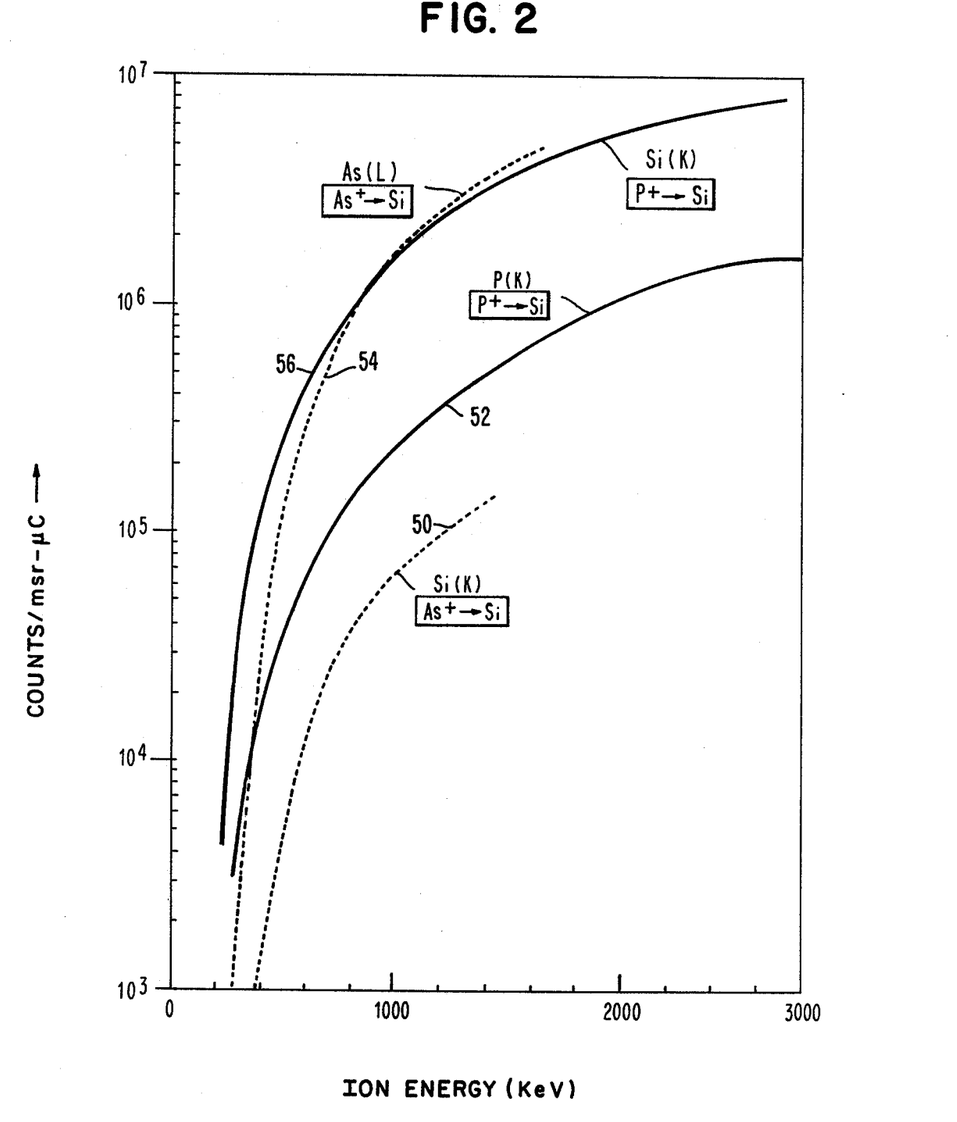
Figure 3:
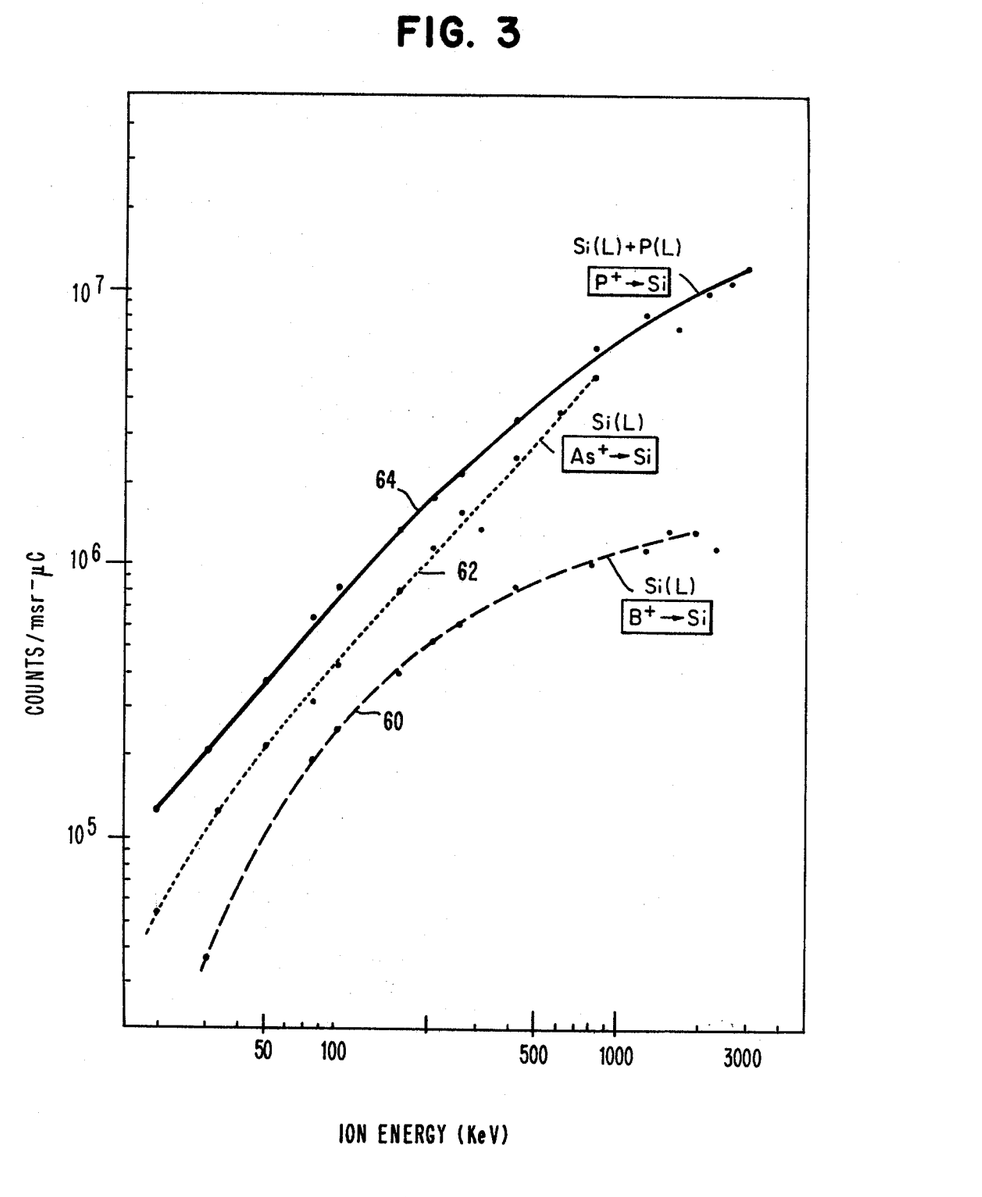

Curves of the high energy X-ray yield vs ion energy obtained for ion beams of $B^+$, $P^+$, and $As^+$ for the practice of this invention are given in FIGS. 2 and 3. These yields for thick targets cannot be easily converted to cross-sections as both the self-absorption of Si for its own Si(L) X-rays and the stopping power of heavy ions in Si are not sufficiently known. The limitation of not having absolute cross-sections does not affect the use of the technique of using X-ray yield to monitor ion implantation dose for high current situations, or in the use of low dose implants discussed before. In both cases the X-ray yield may be correlated with ion dose at moderate currents ($\sim$ 1 microampere) and then the X-ray yield is calibrated for the actual implantation current. For high current applications, the detector 42 must be apertured down to decrease the detection rate to levels below 5000/sec to prevent pile-up effects.

FIG. 2 presents data on measurements by curves 50, 52, 54 and 56 of the number of counts detected X-rays per millisteradian per microcoulomb of ion charge intercepted by the target for Si(K) from ($As^+ \rightarrow$ Si), P(K) from ($P^+ \rightarrow$ Si), As(L) from ($As^+ \rightarrow$ Si) and Si(K) from ($P^+ \rightarrow$ Si) respectively.

The curves 60, 62 and 64 in FIG. 3 present data on measurements of the number of counts of emitted X-rays per millisteradian per microcoulomb of ion charge intercepted by the target for Si(L) from ($B^+ \rightarrow$ Si), Si(L) from ($As^+ \rightarrow$ Si) and Si(L) + P(L) from ($P^+ \rightarrow$ Si) respectively. These are thick target yields because the ion beams were stopped within the target. Because the self-absorption of soft Si(L) X-rays by Si is not known, these yields cannot be considered as cross-sections.

Ion dose monitoring is especially useful for very low and very high ion beam currents in two circumstances. Very low currents, i.e. $\lesssim 10^{-9}$ Amperes, with ion implantation doses below $10^{12} cm^{-2}$ are suitable for threshold shifts in field-effect transistors but are susceptible to errors due to noise pick-up. Very high currents ($\gtrsim 10^{-3}$A) are used for fabrication of bipolar emitters and these currents may be neutralized by the injection of electrons so that space-charge effects will not dilate the beam. However, the presence of electrons may distort the accuracy of charge collection.

There will be some Si damage produced during ion-implantation which may have an effect on the Si(L) yield. However, this is not considered likely since the self-absorption of Si on Si(L) soft X-rays should not be significantly affected by slight shifts in binding energies.

For the doses for practice of this invention in normal ion implantation in Si, i.e., for $\lesssim 1\%$ impurity concentrations, it is not expected that there will be any dose effects on the X-ray yield. The especially useful X-rays considered for the practice of this invention are from the Si substrate, and these will not change in yield until impurity levels reach well above $5 \times 10^{20}$ ions/cm$^2$, which is unusually high for normal practice in ion implantation.

FIG. 3 shows that yield of Si(L) at energies of 50 keV is very high. Illustratively, consider the very low current application of a 0.1 nanoampere beam of As+ at 50 keV, i.e., a current of $6 \times 10^8$ atoms/sec, which is a level sensitive to accelerator noise. This implantation current will provide an Si(L) X-ray yield of 440 counts/sec for a detector solid angle of 22 msr.

Figure 4:
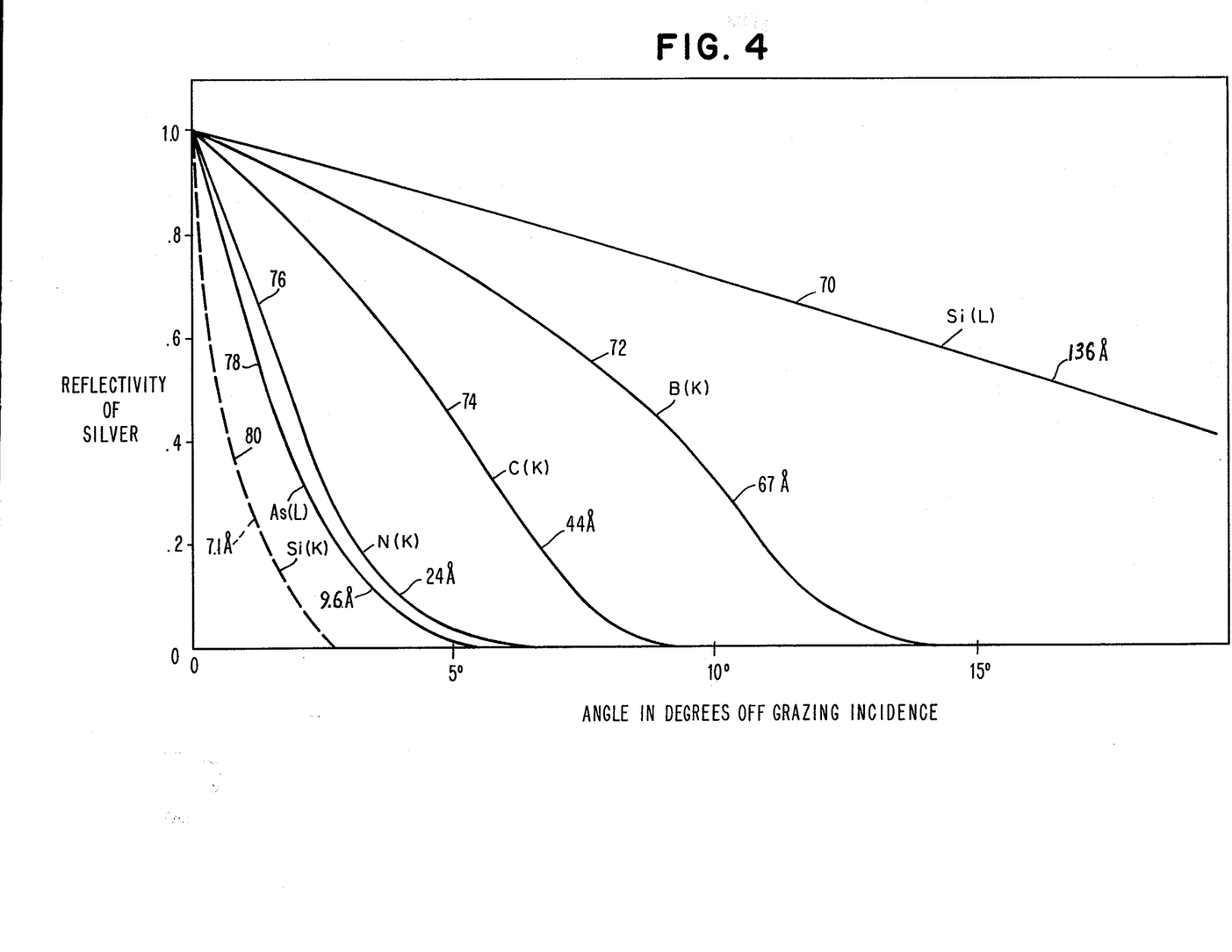
FIG. 4 shows the reflectivity versus angle off grazing incidence for X-rays reflected from a film of silver.

A flow proportional counter has relatively poor energy resolution. Therefore, the monitoring of the X-rays produced by ion implantation is greatly facilitated by X-ray filters which selectively transmit either the low energy long wavelength radiation or the high energy short wavelength radiation. They depend for their operation on the strong wavelength dependence of the specular reflectivity of X-rays from metals. This dependence is shown in FIG. 4 for the reflectivity of X-rays of various wavelengths from a film of silver. The utilization of this property in a long wavelength transmitting filter is shown in FIG. 5.

The curves 70, 72, 74, 76, 78 and 80 of FIG. 4 are examples of typical literature data on the reflectivity of X-rays, e.g., X-rays of As(L) (curve 78) or B(K) (curve 72) from a film of silver. The curve 70 for Si(L) emitted low energy soft X-rays is readily distinguishable from curve 80 for Si(K) emitted high energy X-rays.

Figure 5:
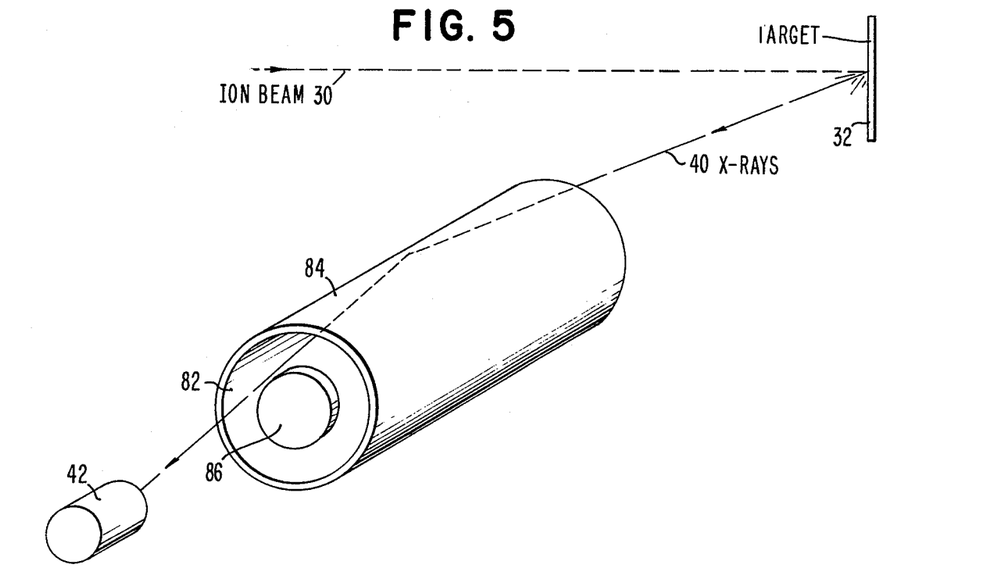
FIG. 5 shows a device for selecting the X-rays to be monitored, e.g. preferentially selecting Si(L) low energy soft X-rays over Si(K) high energy X-rays.

FIG. 5 shows the same arrangement as in FIG. 1B of ion beam 30, target 32, emitted X-rays 40 and detector 42. A cylindrical quartz tube 84 is silvered on the inside with film of silver 82. Quartz tube 84 is aligned coaxially between the target 32 and detector 42 on the path of the emitted X-rays. At the exit aperture, a shield 86 prevents incident X-rays from target 32 from directly striking detector 42. The angle of incidence is selected in accordance with the parameters of FIG. 4 to maximize the reflectivity of particular X-rays to be monitored at detector 42. This arrangement is particularly suited to the detection of long wavelength X-rays and the reduction of the number of short wavelength X-rays which reach the detector. For transmitting short wavelengths selectively, the cylinder 84 is replaced by a 1 mill Be foil established between the target 32 and detector 42.

Figure 6:
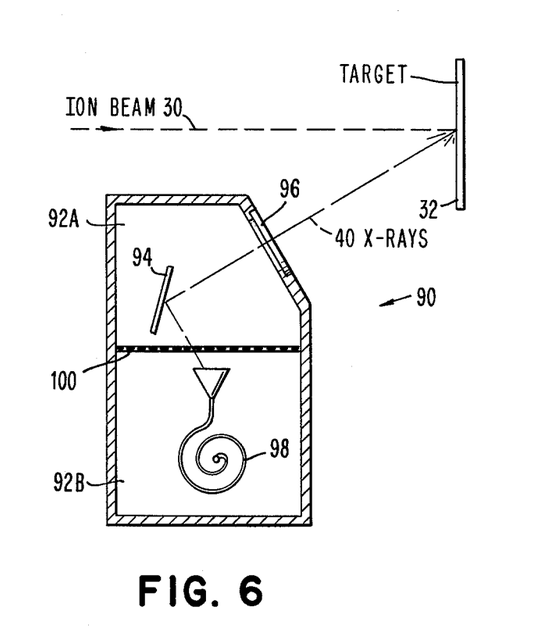
FIG. 6 shows a device incorporating a channeltron X-ray detector which is especially suitable for detecting long wavelength soft X-rays.

It is feasible to replace the flow proportional counter with an electron multiplier device whose cathode has desirable photoelectric yield in the soft X-ray region. An embodiment of this device is shown in FIG. 6. This device has simpler electronics and better vacuum properties than the flow proportional counter. Thus, FIG. 6 presents a detector 90 especially suitable for long wavelength soft X-rays. It comprises a chamber 92A within which is placed a silver mirror surface 94. A replaceable polypropylene entrance window 96 is transparent to X-rays 40 which enter chamber 92A and are reflected from silver mirror surface 94. The window 96 prevents sputtering from target 32 onto mirror 94. A channel-electron-multiplier X-ray detector 98 is located in chamber 92B and is separated from mirror 94 by a grid 100 to repel any ions which may accompany the X-rays to be monitored. The detector 98 is described in the literature, e.g., in the journal articles: Applied Optics, Vol. 9, page 505, 1970, by C. S. Weller et al. It operates on the principle photoelectric electron emission. A current is obtained which is accurately related to the number of incident long wavelength soft X-rays.

Figure 7:
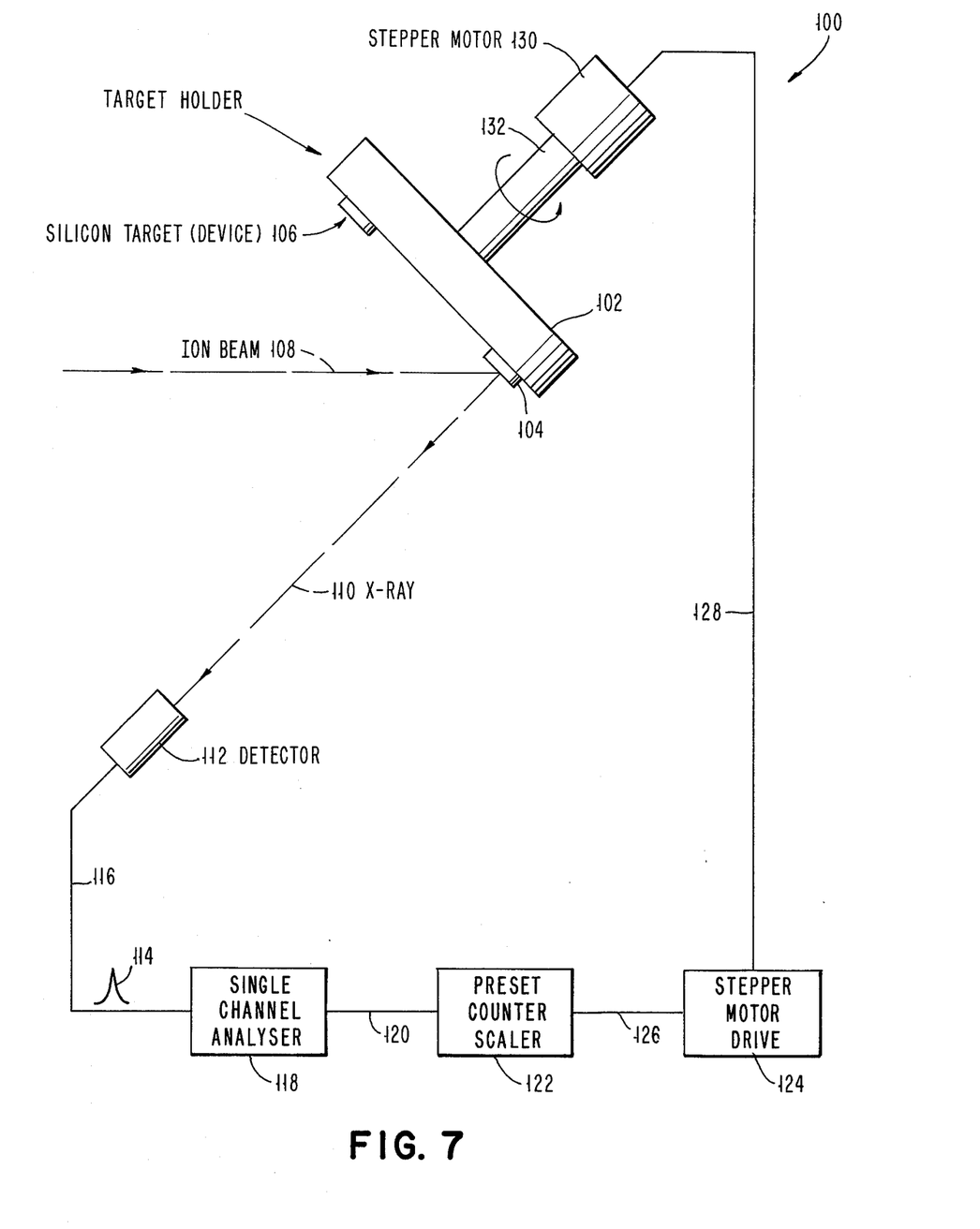
FIG. 7 is a line and block diagram illustrating a control system for controlling both target location and ion dose for the practice of this invention in fabricating semiconductor integrated circuit device, e.g., the emitter region of a bipolar transistor or the gate region of a field effect transistor.

FIG. 7 presents schematically a line and block diagram of a control system 100 for ion implantation for semiconductor device fabrication. The system 100 comprises a moveable target holder 102 with two exemplary Si semiconductor devices 104 and 106 mounted thereon. Ion beam 108 is shown being implanted into device 104. X-rays 110 from target device 104 are presented to detector 112 which produces one current pulse per detected X-ray on connection 116 to single channel analyzer 118. A preset counter 122 is driven by single channel analyzer 118 via connection 120. Stepper motor drive unit 124 is operated by preset counter scalar 122 via connection 126. After a given present number N of output pulses, stepper motor drive 124 actuates via connection 128 stepper motor 130 which via shaft 132 rotates target holder 102 so that device 106 replaces device 104 in the ion beam 108. Illustratively, semiconductor devices 104 and 106 may be a plurality of substantially identical bipolar or field effect transistors in which the emitter regions or gate regions respectively are to be obtained by ion implantation.

CONSIDERATIONS FOR THE INVENTION

The following Table I relates the description for a particular type of emitted X-ray to the wavelength thereof.

TABLE I

| X-ray | λ | Energy (e.v.) |
|---|---|---|
| Si(L) | 136Å | 91.5 |
| As(L) | 9.6Å | 1282 |
| P(L) | 104Å | 119 |
| P(K) | 6.2Å | 2013 |
| B(K) | 67Å | 184 |
| Si(K) | 7.1Å | 1740 |

An exemplary practice of this invention for monitoring dose of ion implantation will be described for ions As+ into Si using curve 62 of FIG. 3. For ions of As+ with energy of 100 Kev, by the curve 62, the number of X-rays/msr/$\mu$C is $\approx 4 \times 10^5$. Thus, for $4 \times 10^5$ counts, and as coulomb = $6.25 \times 10^{18}$ charges, if there is a dose of $10^{11}$ ions/cm$^2$ to target, the result is $4.5/6.25 \times 10^5$ X-rays.

Heretofore the low energy soft Si(L) X-rays which occurred during ion implantation have not been studied because the 134Å X-rays are so low in energy that only a carefully designed flow proportional counter will detect them above the inherent detector noise. Ion implantation is usually carried out in the 30–250 Kev energy range where the high energy X-rays, e.g., Si(K) have such low yields (X-rays/ion) that X-rays were not considered to be sufficiently available for ion implant dose monitoring.

It has been shown for the practice of this invention that the yield of Si(L) X-rays whose production by heavy ion bombardment cannot as yet be predicted is actually copious. Previous X-ray measurements for the purpose of identification of the silicon spectra were carried out by electron or photon excitation and cannot be extrapolated to heavy ion excitation. These low energy soft X-rays do not depend on the charge (or neutrality) of the incident ion (projectile). They are the same for incident neutral as well as multiply ionized projectiles, as has been demonstrated for the practice of this invention.

Practice of this invention includes the use of these low energy X-rays with suitable filters, e.g., mirror + 1$\mu$m polypropylene layer, to select the Si(L) X-rays for the purpose of monitoring the number of incident implant ions (projectiles) thereby obtaining reproducible semiconductor devices.

Additionally, practice of this invention includes use of the X-rays of the high energy incident ion P(K), B(K), As(L), or the Si(K) X-rays for the monitoring of ion dose when the incident ion beam is in the high energy range, i.e. ≥ 300 Kev.

What is claimed is:

1. Method of monitoring dose of ions implanted into a target comprising the steps of:
   providing a target for ion implantation;
   providing a beam of ions to said target;
   selecting x-rays emitted from said target for counting;
      wherein said selected x-rays are from the spectrum which includes low energy soft x-rays; and
   counting said selected X-rays as a measure of the dose of ions implanted therein.

2. Method as set forth in claim 1 wherein said target is Si and said ions are selected from the class consisting of $As^+$, $P^+$ and $B^+$.

3. Method as set forth in claim 2 wherein said target is a Si semiconductor device.

4. Method as set forth in claim 2 wherein said target is a Si semiconductor transistor selected from the class consisting of bipolar field-effect transistors.

5. Method as set forth in claim 2 wherein said monitored X-rays are selected from the class consisting of Si(L) and Si(K) X-rays.

6. Method as set forth in claim 2 wherein said implanted ions are $As^+$ and said monitored X-rays are selected from the group consisting of Si(L), Si(K), As(L) and As(K) X-rays.

7. Method as set forth in claim 2 wherein said implanted ions are $P^+$ and said monitored X-rays are selected from the class consisting of Si(L), Si(K), and Si(L) plug P(L) X-rays.

8. Method as set forth in claim 2 wherein said implanted ions are $B^+$ and said monitored X-rays are selected from the class consisting of Si(L), Si(K) and B(K).

9. A system for implating a given ion dose from an ion beam into a selected target comprising:
   a holder for a plurality of targets;
   means for establishing said targets selectively in the path of said ion beam to obtain characteristic X-rays;
      wherein said characteristic X-rays are from the spectrum which includes low energy soft X-rays;
   X-ray detector means for providing a number of electrical pulses equal to the number of said emitted X-rays;
   means for counting said number of emitted X-rays; and
   means for terminating said implanting of ions in said target when said given ion dose is achieved.

10. A system as set forth in claim 9 wherein said targets are a given semiconductor device.

11. A system as set forth in claim 9 wherein said means for terminating said implanting of said ion dose includes
   a stepper motor operably connected to said target holder; and
   a stepper motor drive circuit operable by said X-ray counting means whereby said one target is transported from the path of said ion beam and said another target of said plurality of targets is transported into the path of said ion beam.

12. A system as set forth in claim 9 wherein said X-ray detector means includes a detector unit for providing one electrical signal for each said detected characteristic X-ray from said selected target, said detector unit being selected from the class consisting of flow-proportional-counter and channel-electron multiplier.

* * * * *

UNITED STATES PATENT AND TRADEMARK OFFICE
CERTIFICATE OF CORRECTION

PATENT NO. : 4,110,625
DATED : Aug. 29, 1978
INVENTOR(S) : J. A. Cairns, A. Lurio, J. F. Ziegler It is certified that error appears in the above–identified patent and that said Letters Patent are hereby corrected as shown below:

Column 7, line 33 delete "plug" and substitute therefor --plus--

Signed and Sealed this

Tenth Day of June 1980

[SEAL]

Attest:

SIDNEY A. DIAMOND

Attesting Officer    Commissioner of Patents and Trademarks